United States Patent [19]

Franke et al.

[11] Patent Number: 4,472,434
[45] Date of Patent: Sep. 18, 1984

[54] ACYL UREAS, INSECTICIDES CONTAINING THESE COMPOUNDS AS WELL AS METHODS FOR THEIR PRODUCTION

[75] Inventors: Heinrich Franke; Hartmut Joppien, both of Berlin, Fed. Rep. of Germany

[73] Assignee: Schering Aktiengesellschaft, Berlin and Bergkamen, Fed. Rep. of Germany

[21] Appl. No.: 325,842

[22] Filed: Nov. 30, 1981

[30] Foreign Application Priority Data

Dec. 8, 1980 [DE] Fed. Rep. of Germany ....... 3046672

[51] Int. Cl.³ .................. A01N 9/20; C07C 127/22
[52] U.S. Cl. ........................................ 424/322; 564/44
[58] Field of Search .......................... 564/44; 424/322

[56] References Cited

U.S. PATENT DOCUMENTS 4,170,657 10/1979 Rigterink .................... 564/44 X
4,276,309 6/1981 Franke et al. .............. 564/44 X
4,427,596 1/1984 Takemoto et al. .......... 564/52 X

*Primary Examiner*—Thomas A. Waltz
*Attorney, Agent, or Firm*—Michael J. Striker

[57] ABSTRACT

New acyl urea of the general formula

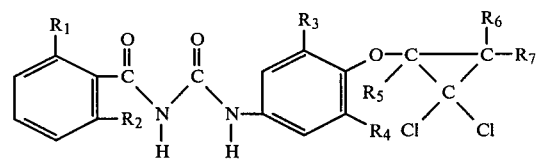

in which
$R_1$ is halogen or $C_1$–$C_6$-alkyl,
$R_2$ is hydrogen or halogen,
$R_3$ is hydrogen, halogen or methyl,
$R_4$ is hydrogen, halogen or methyl, and
$R_5$, $R_6$ and $R_7$ are the same or different and are hydrogen, $C_1$–$C_6$-alkyl or aryl, insecticidal agents containing these compounds as well as methods for their production. The compounds are effective in particular for the control of insect pests belonging to the classes Diptera, Coleoptera, as well as Lepidoptera.

21 Claims, No Drawings

ACYL UREAS, INSECTICIDES CONTAINING THESE COMPOUNDS AS WELL AS METHODS FOR THEIR PRODUCTION

BACKGROUND OF THE INVENTION

The invention concerns new acyl ureas, insecticides containing these compounds as well methods for their production.

1-acyl-3-phenylurea with insecticidal activity is already known from German Patent DE-OS No. 2 123 236. Their activity is, however, not always satisfactory.

SUMMARY OF THE INVENTION

It is therefore the object of the present invention to provide an insecticide which controls insects more successfully than the known compounds.

This object is attained according to the present invention by an insecticide characterized by a content of one or more compounds of the general formula

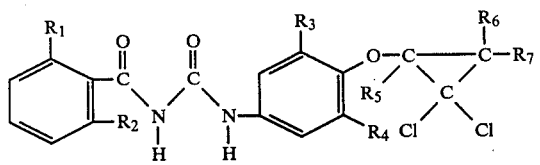

in which $R_1$ is halogen or $C_1$–$C_6$-alkyl, $R_2$ is hydrogen or halogen, $R_3$ is hydrogen, halogen or methyl, $R_4$ is hydrogen, halogen or methyl, and $R_5$, $R_6$ and $R_7$ are the same or different and are hydrogen, $C_1$–$C_6$-alkyl or aryl.

The designation $C_1$–$C_6$-alkyl encompasses, for example, the radicals methyl, ethyl, propyl, isopropyl, butyl, isobutyl, pentyl and hexyl.

Aryl includes, for example, phenyl or substituted phenyl, such as chlorphenyl, and halogen represents fluorine, chlorine, bromine or iodine.

The compounds according to the present invention display in surprising manner an insecticidal activity superior in comparison to the known structurally analogous active agents, or other advantages with regard to the control of various determined insects.

An outstanding selective insecticidal activity is displayed by the compounds according to the present invention against significant harmful insects, in particular those belonging to the classes Diptera, Coleoptera, as well as Lepidoptera.

The use of the compounds according to the present invention can follow in concentrations of about 0.0005 to 5.0%, preferably from 0.001 to 0.1%.

The compounds according to the present invention can be used either alone, in mixture with one another, or with other insecticidal agents. If necessary, other plant protection or parasite control agents, such as for example acarizides or fungicides, can be added according to the desired purpose.

A promotion of the intensity and speed of activity can be obtained, for example, with activity increasing additives, such as organic solvents, wetting agents and oils. Such additives accordingly allow, if necessary, a decrease in the dosaging of the active agent.

The characterized active agents, or mixtures thereof, are expediently used in the form of preparations such as powders, dusting agents, granulates, solutions, emulsions or suspensions, with the addition of liquid and/or solid carriers, or diluting agents and, if necessary, wetting, adhesion, emulsifying and/or dispersing adjuvants.

Suitable liquid carriers include, for example, water, aliphatic and aromatic hydrocarbons, futhermore cyclohexanone, isophorone, dimethylsulfoxide, dimethylformamide and mineral oil fractions.

Mineral earths, for example tonsil, silica gel, talc, kaolin, attaclay, limestone, silicic acid, and plant products, for example flour, are suitable as solid carriers.

As surface active substances, the following are mentioned by way of example: calcium, lignin sulfonate, polyoxyethylene-alkylphenylether, naphthalene sulfonic acids and their salts, phenol sulfonic acids and their salts, formaldehyde condensates, fatty alcohol sulfates, as well as substituted benzene sulfonic acids and their salts.

The portion of active agent(s) in the different preparations can vary within wide limits. For example, the agent may contain about 5–80% by weight active substance, about 95–20% liquid or solid carrier, as well as if necessary up to 20% by weight surface active substances, with corresponding decrease in the amount of active agents and/or carrier when surface active agents are used.

Circulation of the agent can follow in customary manner, for example with water as carrier in spray amounts of about 100 to 3,000 liter/ha. Use of the agent in so-called low-volume and ultra-low-volume methods is likewise possible, as is their application in the form of so-called microgranulates.

Production of these preparations can be performed in known manner, for example through milling or mixing methods. If desired, the individual components can also be mixed first briefly before their use, for example, as carried out in practice by the so-called tank mix method.

For production of the preparations, the following components, for example, are added:

(a)
80% by weight active agent
15% by weight kaolin
5% by weight surface active material based upon the sodium salt of N-methyl-N-oleyl-taurine and the calcium salt of lignin sulfonic acid (b)
50% by weight active agent
40% by weight clay minerals
5% by weight cell pitch
5% by weight surface active material based upon a mixture of the calcium salt of lignin sulfonic acid with alkylphenolpolyglycolether (c)
20% by weight active agent
70% by weight clay minerals
5% by weight cell pitch
5% by weight surface active material based upon a mixture of calcium salt of lignin sulfonic acid with alkylphenylpolyglycolether (d)
5% by weight active agent
80% by weight tonsil
10% by weight cell pitch
5% by weight surface active material based upon a fatty acid condensation product Of the compounds according to the present invention, those displaying a particularly good insecticidal activity are those for which in the above given general formula $R_1$ is chlorine or fluorine, $R_2$ is hydrogen, chlorine or fluorine, R₃ is hydrogen, chlorine or methyl, R₄ is hydrogen, chlorine or methyl, and R₅, R₆ and R₇ are the same or different and are hydrogen or methyl.

The compounds according to the present invention may be produced by bringing together for reaction (a) alkoxyaniline of the general formula

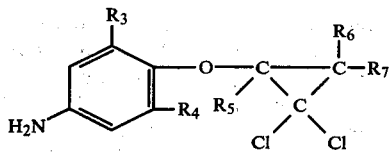

II with benzoylisocyanate of the general formula

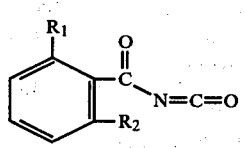

III if necessary with use of a solvent, or (b) reacting alkoxyphenolisocyanate of the general formula

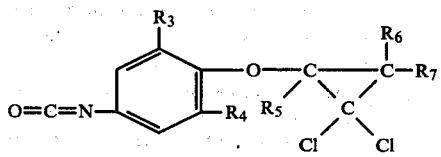

IV with benzamide of the general formula

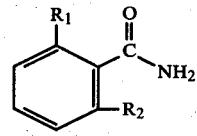

V if necessary in the presence of a solvent, with $R_1$, $R_2$, $R_3$, $R_4$, $R_5$, $R_6$ and $R_7$ having the above given meanings.

As solvent, materials inert in relation to the reactants are suitable, such as aromatic and aliphatic hydrocarbons, if necessary chlorinated, such as toluene, chlorbenzene, chloroform and hexane, ethers, such as diethyl ether and tetrahydrofuran, esters, such as acetic acid ethyl ester, as well as nitriles, such as acetonitrile and benzonitrile.

The reaction temperatures can vary within wide limits. Preferred for method variation (a) is the range from about 20° to 100° C., and with the method variant (b) the range of about 80° to 200° C. The reactions follow in general at normal pressure.

The acylureas according to the present invention are colorless and odorless crystalline compounds. They dissolve only very poorly in water or toluene, better in acetic ester, and well in dimethylformamide.

The novel features which are considered as characteristic for the invention are set forth in particular in the appended claims. The invention itself, however, both as to preparation and method of use, together with additional objects and advantages thereof, will be best understood from the following description of specific embodiments.

DESCRIPTION OF THE PREFERRED EMBODIMENTS

The following example illustrates the production of the compounds according to the present invention.

EXAMPLE 1

1-[4-(2,2-dichlorcyclopropyloxy)-phenyl]-3-(2-methylbenzoyl)-urea 6.54 g (0.03 Mol) of 4-(2,2-dichlorcyclopropyloxy)-aniline, dissolved in 50 ml dry tetrahydrofuran, are added dropwise with 4.84 g (0.03 Mol) of 2-methylbenzoyl-isocyanate, with stirring. The temperature increases mildly therewith. After cooling, the product is precipitated with pentane, withdrawn by suction, after-washed with pentane and dried.

Yield: 8.3 g (74% of theoretical amount)
MP: 175°–176° C.

In analogous manner, the following compounds according to the present invention are produced:

| Compound Name | Physical Constant |
|---|---|
| 1-[3-chlor-4-(2,2-dichlor-3,3-dimethyl-cyclopropyloxy)-phenyl]-3-(2-chlorobenzoyl)-urea | MP: 153° C. (decomposition) |
| 1-[4-(2,2-dichlor-3,3-dimethylcyclopropyl-oxy)-3-methylphenyl]-(2,6-dichlorobenzoyl)-urea | MP: 186–187° C. |
| 1-(2-chlorbenzoyl)-3-[4-(2,2-dichlor-3,3-dimethylcyclopropyloxy)-3-methylphenyl]-urea | MP: 184–185° C. |
| 1-[4-(2,2-dichlor-3,3-dimethylcyclopropyl-oxy)-3-methylphenyl]-3-(2,6-difluorbenzoyl)-urea | MP: 204–205° C. |
| 1-[3-chlor-4-(2,2-dichlor-3,3-dimethyl-cyclopropyloxy)-phenyl]-3-(2,6-difluor-benzoyl)-urea | MP: 200–202° C. |
| 1-[4-(2,2-dichlor-3-methylcyclopropyl-oxy)-3-methylphenyl]-3-(2-methyl-benzoyl)-urea | MP:187–189° C. |
| 1-(2-chlorbenzoyl)-3-[4-(2,2-dichlor-3-methylcyclopropyloxy)-3-methylphenyl]-urea | MP: 170–172° C. |
| 1-[4-(2,2-dichlor-3-methylcyclopropyl-oxy)-3-methylphenyl]-3-(2,6-dichlor-benzoyl)-urea | MP: 165–167° C. |
| 1-(2,6-dichlorbenzoyl)-3-[4-(2,2-dichlorcyclopropyloxy)-phenyl]-urea | MP: 199–200° C. |
| 1-[4-(2,2 dichlorcyclopropyloxy)-phenyl]-3-(2,6-difluorbenzoyl)-urea | MP: 189–190° C. |
| 1-(2-chlorbenzoyl)-3-[4-(2,2-dichlor-cyclopropyloxy)-phenyl]-urea | MP: 160–162° C. |
| 1-(2,-chlorbenzoyl)-3-[4-(2,2-dichlor-cyclopropyloxy)-3,5 dimethylphenyl]-urea | MP: 144–146° C. |
| 1-(2-chlorbenzoyl)-3-[3-chlor-4-(2,2-dichlorcyclopropyloxy)-phenyl]-urea | MP: 195–197° C. |
| 1-[4-(2,2-dichlorcyclopropyloxy)-phenyl]-3-(2-fluorbenzoyl)-urea | MP: 159–161° C. |
| 1-(2-brombenzoyl)-3-[4-(2,2-dichlor-cyclopropyloxy)-phenyl]-urea | MP: 162–165° C. |
| 1-[3-chlor-(2,2-dichlorcyclopropyloxy)-phenyl]-3-(2,6-dichlorbenzoyl)-urea | MP: 205–207° C. |

The benzamide and benzoylisocyanate to be used as starting materials are known, or can be produced according to known methods.

The required aniline is obtained, for example, through reduction of the corresponding nitro-compound(s) according to known methods. These nitro-compounds can be produced, for example, from corresponding phenols through etherification with allyl-halogenides, whereby the resulting phenyl allylethers are then isomerized with strong bases into phenylenolethers. These then give, with dichlorcarbene and subsequent nitrogenation, the desired nitro-compounds.

According to another method, nitrophenols are converted, with acetic acid vinyl ester in the presence of catalytic amounts of mercury acetate and acid, into vinyl ethers, which are then brought into reaction with dichlorcarbene, preferably using the so-called phase transfer method.

The mentioned vinylethers can also be produced in a two-stage reaction, in which the phenols are initially reacted with 1,2-dibromoethane, in the presence of a weak base, into bromoethylether, and these are then dehydrobrominated with a strong base into vinylethers.

The following describes production of one of the starting materials:

4-(2,2-dichlorocyclopropyloxy)-aniline 104 g (0.75 Mol) of 4-nitrophenol are dissolved in 420 ml (4.5 Mol) acetic acid vinyl ester. After washing with nitrogen, successively 3.0 g mercury acetate and 0.2 ml $BF_3$-etherate are added. The reaction mixture is stirred for 4 hours at 50° C. After cooling, 2 g sodium acetate are added, evaporated, and the residue then dissolved in ether. There follows washing three times with 2 n-caustic soda, three times with water, drying and evaporation. The residue is recrystallized from ether. 65 g (52% of theoretical amount) of 4-nitrophenylvinylether are obtained, with a melting point of 59°–61° C.

41.3 g (0.25 Mol) of the vinyl ether and 0.6 g benzyltriethylammonium chloride are dissolved in 150 ml chloroform, and with strong stirring, reacted with 150 ml 50% caustic soda. The reaction mixture is stirred for 5 hours, with the temperature being held, initially through cooling, then through heating, between 55° and 60° C. It is subsequently mixed with 200 ml each of chloroform and water, and filtered across celite. The organic phase is separated, washed with water, dried and evaporated. There remains behind 40 g (64% of theoretical amount) of 4-(2,2-dichlorcyclopropyloxy)-nitrobenzene, as a dark oil, which is used without further purification. $n_D^{20} = 1.5856$.

70 ml ethanol are reacted with 9.7 ml (0.2 Mol) hydrazine hydrate and 5 g Raney-nickel. With stirring, 12.4 g (0.05 Mol) of the cyclopropyloxy-nitrobenzene, dissolved in 20 ml ethanol, are then dripped in; in so doing the interior temperature should not exceed 40° C. The reaction mixture is then after-stirred for an hour, filtered, the filtrate evaporated, and then dissolved in ether. This solution is washed three times with water, dried and evaporated once again. There remains as residue 9 g (82% of theoretical amount) of 4-(2,2-dichlorcyclopropyloxy)-aniline, a brown oil, which is used without further purification. $n_D^{20}$ is 1.5773.

The following example illustrates possibilities of use for the compounds according to the present invention, which follow in the form of their preparations.

EXAMPLE 2

The substances according to the present invention are employed as aqueous suspensions with an active agent concentration of 0.05%.

Bush bean plants (Phaseolus vulgaris) in the primary leaf stage are soaked in these active agent preparations. Four plant stalks with a total of eight primary leaves are put in a glass vase filled with water and then caged in a glass cylinder, for each test.

Five larvae of the Mexican bean beetle (Epilachna varivestis) in the third larval stage are then placed in each glass cylinder, and held therein for 5 days. The criterion for an estimation of effectiveness is the mortality of the larvae, in percent, after a test duration of 5 days.

| Compound According to the Invention | Active Agent Concentration in % | Mortality in % |
| --- | --- | --- |
| 1-[3-chlor-4-(2,2-dichlor-3,3-dimethylcyclopropyloxy)-phenyl]-3-(2-chlorbenzoyl)-urea | 0.05 | 100 |
| 1-[4-(2,2-dichlor-3,3-dimethylcyclopropyloxy)-3-methylphenyl]-3-(2,6-dichlorbenzoyl)-urea | 0.05 | 100 |
| 1-(2-chlorbenzoyl)-3-[4-(2,2-dichlor-3,3-dimethylcyclopropyloxy-3-methylphenyl]-urea | 0.05 | 100 |
| 1-[3-chlor-4-(2,2-dichlor-3,3-dimethylcyclopropyloxy)-phenyl]-3-(2,6-difluorbenzoyl)-urea | 0.05 | 100 |
| 1-[4-(2,2-dichlor-3-methylcyclopropyloxy)-3-methylphenyl]-3-(2-methylbenzoyl)-urea | 0.05 | 100 |
| 1-(2-chlorbenzoyl)-3-[4-(2,2-dichlor-3-methylcyclopropyloxy)-3-methylphenyl]-urea | 0.05 | 100 |
| 1-[4-(2,2-dichlor-3-methylcyclopropyloxy)-3-methylphenyl]-3-(2,6-dichlorbenzoyl)-urea | 0.05 | 100 |
| 1-(2,6-dichlorbenzoyl)-3-[4-(2,2-dichlorcyclopropyloxy)-phenyl]-urea | 0.05 | 100 |
| 1-[4-(2,2-dichlorcyclopropyloxy)-phenyl]-3-(2,6-difluorbenzoyl)-urea | 0.05 | 100 |
| 1-(2-chlorbenzoyl)-3-[4-(2,2-dichlorcyclopropyloxy)-phenyl]-urea | 0.05 | 100 |
| 1-(2-chlorbenzoyl)-3-[4-(2,2-dichlorcyclopropyloxy)-3,5-dimethylphenyl]-urea | 0.05 | 100 |
| 1-(2-chlorbenzoyl)-3-[3-chlor-4-(2,2-dichlorcyclopropyloxy)-phenyl]-urea | 0.05 | 100 |
| 1-(2-brombenzoyl)-3-[4-(2,2-dichlorcyclopropyloxy)-phenyl]-urea | 0.05 | 100 |

EXAMPLE 3

The compounds according to the present invention are applied as aqueous suspensions with an active agent concentration of 0.01%. The comparison agents are used in the same manner. Two cauliflower leaves per test are sprayed with 4 mg active agent preparation per cm², dosed into polystyrene Petrie dishes. After drying of the spray coating, ten young caterpillars, of the so-called cabbage moth species (Plutella maculitennis) are put into each Petrie dish, and exposed to the treated food in the laboratory for 8 days. Criteria for the determination of effectiveness are the mortality of the caterpillars after 2 days, the suppression of consumption of the caterpillars in percent, as well as the prevention of emergence of moth in percent after 8 days. The results are presented in the following table:

| | Active Agent Concentration in % | Mortality in % | Suppression of Consumption in % | Prevention of Moth Emergence in % |
|---|---|---|---|---|
| Compounds According to the Invention | | | | |
| 1-[4-2,2-dichlorcyclopropyloxy)-phenyl]-3-(2,6-difluorbenzoyl)-urea | 0.01 | 75 | 80 | 100 |
| 1-(2-chlorbenzoyl)-3-[4-(2,2-dichlorcyclopropyloxy)-phenyl]-urea | 0.01 | 85 | 70 | 100 |
| COMPARISON AGENT ACCORDING TO DE-OS 2,123,236 | | | | |
| N—(2,6-difluorbenzoyl)-N'—(p-chlorphenyl)-urea | 0.01 | 30 | 50 | 100 |
| N—(2,6-dichlorbenzoyl)-N'—(p-chlorphenyl)-urea | 0.0 | 10 | 30 | 0 |
| UNTREATED CONTROL | 0.0 | 10 | 30 | 0 |

EXAMPLE 4

The compounds according to the present invention are applied as aqueous suspensions with a concentration of active agent of 0.001%. The comparison agents are applied in the same manner. Plant dishes (20×20 cm), containing 25–30 bush bean plants (*Phaseolus vulgaris*) in the primary leaf stage, are sprayed dripping wet with the active agent preparations. The so-treated dishes are placed in a greenhouse for 24 hours. Thereafter, 4 plant stalks with 8 primary leaves are withdrawn per test, placed in glass vases filled with water, and caged in glass cylinders. 5 larvae of the Mexican bean beetle (*Epilachna varivestis*) in the third larval stage are then placed in each glass cylinder, and held there for 6 days.

Criteria for the determination of activity are the mortality and the suppression of consumption of the larvae in percent after a test duration of 6 days.

| | Active Agent Concentration in % | Mortality in % | Suppression of Consumption in % |
|---|---|---|---|
| Compounds According to the Invention | | | |
| 1-(2-chlorbenzoyl)-3-[4-(2,2-dichlor-3-methylcyclopropyloxy)-3-methyl-phenyl]-urea | 0.001 | 100 | 80 |
| 1-[4-(2,2-dichlorcyclopropyloxy)-phenyl]-3-(2,6-difluorbenzoyl)-urea | 0.001 | 100 | 80 |
| 1-(2-chlorbenzoyl)-3-[4-(2,2-dichlor-cyclopropyloxy)-phenyl]-urea | 0.001 | 100 | 80 |
| COMPARISON AGENT according to DE-OS 2,123,236 | | | |
| N—(2,6-difluorbenzoyl)-N'—(p-chlorphenyl)-urea | 0.001 | 60 | 30 |
| UNTREATED CONTROL | 0.0 | 0 | 0 |

It will be understood that each of the elements described above, or two or more together, may also find a useful application in other types of pest control differing from the types described above.

While the invention has been illustrated and described as embodied in acyl ureas, insecticides containing these compounds, as well as methods for their production, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Acyl urea of the general formula

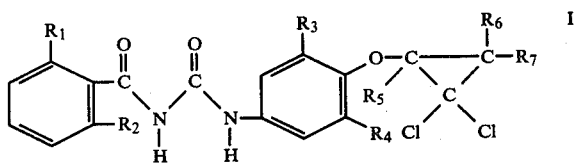

in which
  $R_1$ is halogen or $C_1$–$C_6$-alkyl,
  $R_2$ is hydrogen or halogen,
  $R_3$ is hydrogen, halogen or methyl,
  $R_4$ is hydrogen, halogen or methyl, and
  $R_5$, $R_6$ and $R_7$ are the same or different and are hydrogen, $C_1$–$C_6$-alkyl or aryl.

2. Acyl urea according to claim 1, wherein $R_1$ is chlorine or fluorine, $R_2$ is hydrogen, chlorine or fluorine, $R_3$ is hydrogen, chlorine or methyl, $R_4$ is hydrogen, chlorine or methyl, and $R_5$, $R_6$ and $R_7$ are the same or different and are hydrogen or methyl.

3. The compound according to claim 1, which is 1-[4-(2,2-dichlorcyclopropyloxy)-phenyl]-3-(2-methyl-benzoyl)-urea.

4. The compound according to claim 1, which is 1-[3-chlor-4-(2,2-dichlor-3,3-dimethylcyclopropyloxy)-phenyl]-3-(2-chlorbenzoyl)-urea.

5. The compound according to claim 1, which is 1-[4-(2,2-dichlor-3,3-dimethylcyclopropyloxy)-3-methylphenyl]-3-(2,6-dichlorbenzoyl)-urea.

6. The compound according to claim 1, which is 1-(2-chlorbenzoyl)-3-[4-(2,2-dichlor-3,3-dimethylcyclopropyloxy)-3-methylphenyl]-urea.

7. The compound according to claim 1, which is 1-[4-(2,2-dichlor-3,3-dimethylcyclopropyloxy)-3-methylphenyl]-3-(2,6-difluorbenzoyl)-urea.

8. The compound according to claim 1, which is 1-[3-chlor-4-(2,2-dichlor-3,3-dimethylcyclopropyloxy)-phenyl]-3-(2,6-difluorbenzoyl)-urea.

9. The compound according to claim 1, which is 1-[4-(2,2-dichlor-3-methylcyclopropyloxy)-3-methylphenyl]-3-(2-methylbenzoyl)-urea.

10. The compound according to claim 1, which is 1-(2-chlorbenzoyl)-3-[4-(2,2-dichlor-3-methylcyclopropyloxy)-3-methylphenyl]-urea.

11. The compound according to claim 1, which is 1-[4-(2,2-dichlor-3-methylcyclopropyloxy)-3-methylphenyl]-3-(2,6-dichlorbenzoyl)-urea.

12. The compound according to claim 1, which is 1-(2,6-dichlorbenzoyl)-3-[4-(2,2-dichlorcyclopropyloxy)-phenyl]-urea.

13. The compound according to claim 1, which is 1-[4-(2,2-dichlorcyclopropyloxy)-phenyl]-3-(2,6-difluorbenzoyl)-urea.

14. The compound according to claim 1, which is 1-(2-chlorbenzoyl)-3-[4-(2,2-dichlorcyclopropyloxy)-phenyl]-urea.

15. The compound according to claim 1, which is 1-(2-chlorbenzoyl)-3-[4-(2,2-dichlorcyclopropyloxy)-3,5-dimethylphenyl]-urea.

16. The compound according to claim 1, which is 1-(2-chlorbenzoyl)-3-[3-chlor-4-(2,2-dichlorcyclopropyloxy)-phenyl]-urea.

17. The compound according to claim 1, which is 1-[4-(2,2-dichlorcyclopropyloxy)-phenyl]-3-(2-fluorbenzoyl)-urea.

18. The compound according to claim 1, which is 1-(2-bromobenzoyl)-3-[4-(2,2-dichlorcyclopropyloxy)-phenyl]-urea.

19. The compound according to claim 1, which is 1-[3-chlor-(2,2-dichlorcyclopropyloxy)-phenyl]-3-(2,6-dichlorbenzoyl)-urea.

20. An agent for killing the Mexican bean beetle, comprising an effective amount of one or more compounds according to claim 1, in an appropriate carrier.

21. Insecticidal agent according to claim 20, in mixture with adjuvant material.

* * * * *